US00PP08648P

United States Patent [19]

Goffreda et al.

[11] Patent Number: Plant 8,648

[45] Date of Patent: Mar. 22, 1994

[54] APPLE TREE 'NJ 55'

[75] Inventors: Joseph C. Goffreda, Kendall Park; Anna M. Voordeckers, East Windsor, both of N.J.

[73] Assignee: Rutgers University, New Brunswick, N.J.

[21] Appl. No.: 903,244

[22] Filed: Jun. 18, 1992

[51] Int. Cl.[5] ..... A01H 5/00

[52] U.S. Cl. ..... Plt./34.1

[58] Field of Search ..... Plt. 34.1, 35, 35.1

*Primary Examiner*—James R. Feyrer
*Assistant Examiner*—E. F. McElwain
*Attorney, Agent, or Firm*—Frank B. Robb

[57] ABSTRACT

A new Apple Tree cultivar of the Golden Delicious type, producing fruit of excellent dessert quality and keeping ability, in refrigerated storage.

1 Drawing Sheet

BACKGROUND OF THE DISCLOSURE

This invention relates to a new and distinct cultivar of Apple Tree, developed near Cream Ridge, N.J., as part of certain efforts to develop improved apple trees having improved fruit quality.

The cultivar of this invention is a seedling whose parentage is derived from a block planted in 1964 near Cream Ridge, N.J., in an orchard of other trees whose breeding records are kept.

The new cultivar which we have chosen to designate as NJ55, is a seedling produced by crossing a seedling known as NJ 303955, being the seed parent, and another cultivar "Golden Delicious" which is unpatented, being the pollen parent.

We have found during continued experimentation and growth of the trees of this cultivar that it produces a vigorous, medium upright tree with good crops borne on numerous short axillary branches.

The tree flowers at about the same time as the cultivar known as "Golden Delicious", and the apple fruit produced has excellent quality and hold texture which quality will be maintained for at least five months during refrigerated storage at 34 degrees F. (1 degree C.).

During the course of the several years of observing the growth it is noted that the selection was asexually propagated by us by grafting on seedling apple roots near Cream Ridge, N.J. and on several different dwarfing rootstocks.

The selected one was of grafted material which has maintained the desired characteristics after propagation in successive generations.

Figure 1:
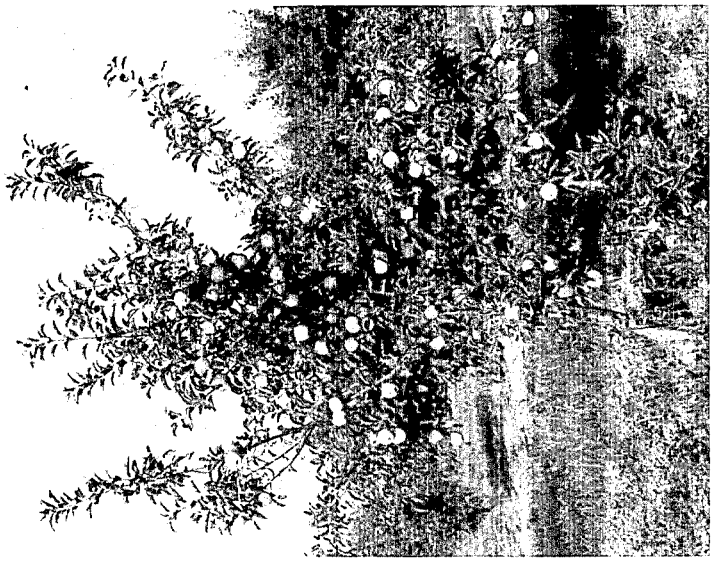

In order to support the disclosure herein, there is provided a drawing wherein FIG. 1 shows a typical example of young tree of the new cultivar illustrating the growth habit thereof, at or about the time when picking would normally be effected.

Figure 2:
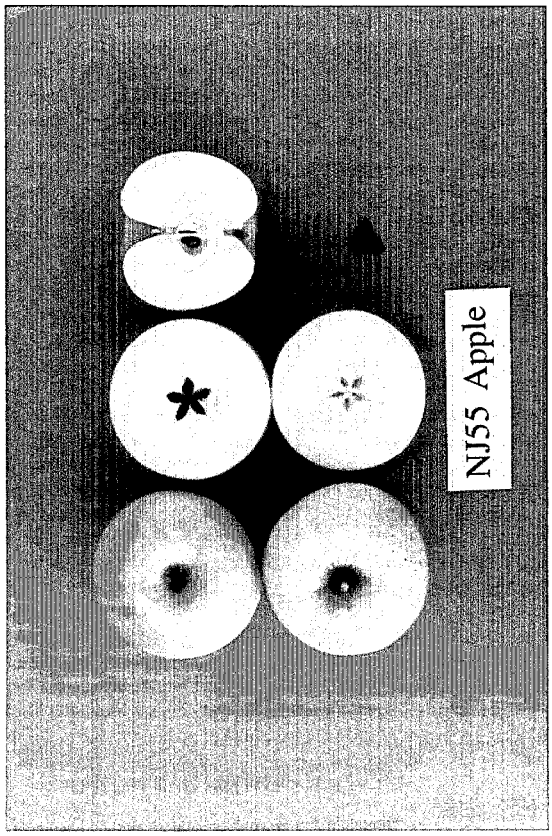

FIG. 2 shows a typical example of the apple produced, disclosing the color, round conical shape, flesh color and blush with the skin color.

In order to described the tree and fruit in particular detail, reference is had to a color chart, known as the Horticultural Color Chart issued by the British Color Council in collaboration with The Royal Horticultural Society, the photographs of which the above are representations being as nearly like the actual fruit and tree as is possible to make the same in a color reproduction of this kind.

Turning to a consideration of the details of this new cultivar, we note that the following description is a detailed description and embodies primary distinctive characteristics and identifying means by which the tree is recognized and the fruit produced is described.

Where color is referred to hereinafter it was measured in terms of its color space coordinates (L*a*b*) with a Minolta CR-300 Chroma Meter calibrated with a white calibration plate.

FLOWER

Petals: 2.2 cm (0.9 inch) in length and 1.2 cm (0.5 inch) in width.

Corolla: 3.9 cm (1.5 inch) in diameter at anthesis.

Color: Flower buds are crimson Plate 59a (L=25.66; a=+30.60; b=+6.60); fading to white, open flowers.

FRUIT

Shape: Round-conic; slightly irregular.

Size: Axial diameter 7.0 cm (2.75 inches); transverse diameter 8.0 cm (3.15 inches).

Color: Undercolor is yellow-green (Plate 153d; L=75.47 a=12.04 b=+46.76). Overcolor is orange-red (Plate 34b to 34c; L=62.35 a=+18.72 b=+36.34) covering between 0 and 40%.

Skin: Slightly rough, with some small light brown irregular dots (lenticels) mostly on the fruit shoulder; medium thick.

Stem: Medium, 1.5 to 2 cm (0.6 to 0.8 inch), medium thick, and clubbed.

Cavity: Acuminate, deep, medium in width, slight to moderate russet.

Basin: Medium in depth, slightly furrowed, wide in breadth.

Calyx: Persistent, erect, partly open, with divergent calyx tips.

Calyx tube: Short, funnel shape.

Stamen remnants: Marginal.

Core: Median position.

Core lines: Clasping, distinct.

Carpels: Axile, closed in cross section; obovate in logitudinal section.

Seeds: Acuminate, plump, not tufted.

Flesh:

*Texture.*—Medium to coarse, crisp, breaking, firm.

*Quality.*—Sweet, mild subacid, rich aromatic flavor, excellent dessert quality.

*Color.*—Naples yellow (Plate 11c).

*Aroma.*—Slight.

Maturity: 1 week after "Golden Delicious".

Keeping quality: Excellent, retains quality and texture for at least 5 months in refrigerated storage at 34 degrees F.

Use: Late maturity, long storage, dessert apple.

TREE

Tree: Medium, upright to semi-erect, very productive, precocious. The size of the original plant on its own roots, at full maturity is about 22′ high and 16′ wide.

On Malling 7-A rootstock the trees at maturity are about 12′ high and 8′ wide.

Leaves: Elliptic, serrate, length to width ratio=2.0.

We claim:

1. A new and distinct Apple Tree cultivar, substantially as herein shown and described, characterized particularly as to novelty by the vigorous, medium upright growth habit of the tree, on standard rootstock, good crop production borne on short axillary branches, excellent keeping and dessert quality of the fruit, which is of medium coarse, flesh-texture, and large round-conic shape, with slight stem russetting, 0–40% blush.

* * * * *